United States Patent
Misumi et al.

(10) Patent No.: US 6,248,857 B1
(45) Date of Patent: Jun. 19, 2001

(54) AROMATIC POLYCARBODIIMIDE AND POLYCARBODIIMIDE SHEET

(75) Inventors: Sadahito Misumi; Akiko Matsumura; Amane Mochizuki; Michio Satsuma; Michie Sakamoto, all of Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 09/404,194

(22) Filed: Sep. 23, 1999

(30) Foreign Application Priority Data

| Oct. 1, 1998 | (JP) | 10-296018 |
| Oct. 27, 1998 | (JP) | 10-305201 |
| Oct. 27, 1998 | (JP) | 10-305205 |

(51) Int. Cl.$^7$ .............. C08G 73/00; C08G 18/02
(52) U.S. Cl. .............. 528/170; 528/44; 528/48; 528/52; 528/173; 528/174; 528/220; 528/224; 528/310; 528/322; 528/350; 528/351; 528/353; 428/473.5
(58) Field of Search ............... 528/44, 173, 48, 528/174, 52, 220, 170, 310, 224, 322, 350, 353, 351; 428/473.5

(56) References Cited

U.S. PATENT DOCUMENTS

| 3,922,143 | * 11/1975 | Schuster et al. ............. 8/94.21 |
| 4,110,302 | 8/1978 | Thomas et al. ............. 260/40 R |
| 4,128,599 | 12/1978 | Thomas et al. ............. 260/857 |
| 4,263,221 | 4/1981 | Schnabel et al. ............. 260/453 |
| 6,008,311 | 12/1999 | Sakumoto et al. ............. 528/74 |
| 6,051,677 | * 4/2000 | Maeda et al. ............. 528/170 |

FOREIGN PATENT DOCUMENTS

| 26 42 577A | 4/1977 | (DE) . |
| 0 411 461A | 2/1991 | (EP) . |
| 47-36278 | 9/1972 | (JP) . |
| 56-50963 | 12/1981 | (JP) . |
| 3-62814 | 3/1991 | (JP) . |
| 9-235341A | 9/1997 | (JP) . |

OTHER PUBLICATIONS

G. Greber et al., A New Synthesis of Isocyanates and Isothiocyanates, Angew. Chem Internat Edit vol. 7 (1968) No. 12, p. 941. The month in the date of publication is not available.

Tod W. Campbell et al., "Carbodiimides. IV. High Polymers Containing the Carbodiimide Repeat Unit" Journal of American Chemical Society, vol. 28, pp. 2069–2075 (1963). The month in the date of publication is not available.

Donald J. Lyman et al., "Polycarbodiimides and their Derivatives" Die Makromolekulare Chemie., vol. 63, pp. 1–9, 1963. The month in the date of publication is not available.

B.M. Shinde et al. "Synthesis and Reactivities of Diisocyanates and Polyamides Therefrom" J. Polym Mater. 6, pp. 25–30 (1989). The month in the date of publication is not available.

* cited by examiner

*Primary Examiner*—P. Hampton-Hightower
(74) *Attorney, Agent, or Firm*—Sughrue, Mion, Zinn, Macpeak & Seas, PLLC (57) ABSTRACT

An aromatic polycarbodiimide comprising a structure represented by the following formula (1) has excellent low moisture resistance, heat resistance and a low dielectric constant:

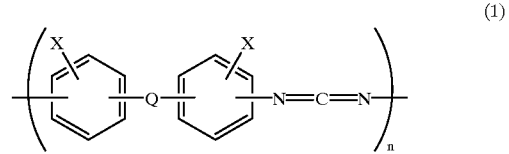

wherein Q is one selected from the group consisting of —$CH_2$—,

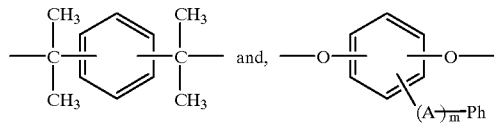

m is 0 or 1, A is a divalent organic group having 4 or less carbon atoms, Ph is a phenyl group, X's are a hydrogen atom when Q is

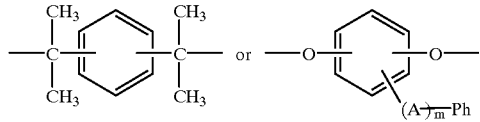

and the same or different halogen atoms when Q is —$CH_2$—, and n is an integer of 2 to 300.

9 Claims, 4 Drawing Sheets

AROMATIC POLYCARBODIIMIDE AND POLYCARBODIIMIDE SHEET

BACKGROUND OF THE INVENTION

1. Field of the Invention

The present invention relates to an aromatic polycarbodiimide and a polycarbodiimide sheet. More particularly, the present invention relates to an aromatic polycarbodiimide having high heat resistance, low hygroscopicity and a low dielectric constant and to a sheet made from such an aromatic polycarbodiimide.

2. Description of the Related Art

There have been known aromatic polycarbodiimides produced by polymerizing diphenylmethane diisocyanate (MDI) or tolylene diisocyanate (TDI) as a monomer. These aromatic polycarbodiimides are used as flame resistant films or heat resistant adhesives because of their excellent heat resistance.

From the point of view that these aromatic polycarbodiimide films do not generate a volatile gas or decomposed monomer even when they are exposed to a temperature higher than 400° C., it can be said that these aromatic polycarbodiimide films have acceptable heat resistance. However, they have low moisture resistance, and loses self supporting properties and become fragile when they are heat-treated at 200° C. or more, so that they are not fit for practical use. In addition, they have poor solubility in an organic solvent and low workability.

SUMMARY OF THE INVENTION

The inventors of the present invention have conducted intensive studies on various raw material monomers and aromatic polycarbodiimides to obviate the above defects of the conventional polycarbodiimides. As a result, they have found that the above problems can be solved by a polycarbodiimide having the following new skeleton and accomplished the present invention based on this finding.

1) In a first aspect, the present invention provides an aromatic polycarbodiimide comprising a structure represented by the following formula (1):

$$\left( \underset{X}{\overset{X}{\bigcirc}} - Q - \underset{X}{\overset{X}{\bigcirc}} - N=C=N \right)_n \tag{1}$$

wherein Q is one selected from the group consisting of —CH$_2$—, $$-\underset{CH_3}{\overset{CH_3}{\underset{|}{C}}} - \bigcirc - \underset{CH_3}{\overset{CH_3}{\underset{|}{C}}} - \text{ and, } -O - \bigcirc_{(A)_m-Ph} - O-$$

m is 0 or 1, A is a divalent organic group having 4 or less carbon atoms, Ph is a phenyl group, X's are a hydrogen atom when Q is $$-\underset{CH_3}{\overset{CH_3}{\underset{|}{C}}} - \bigcirc - \underset{CH_3}{\overset{CH_3}{\underset{|}{C}}} - \text{ or } -O - \bigcirc_{(A)_m-Ph} - O-$$

and the same or different halogen atoms when Q is —CH$_2$—, and n is an integer of 2 to 300.

2) The aromatic polycarbodiimide according to 1) above, which the structure represented by the above formula (1) may be contained in an amount of more than 10 mol %.

3) The aromatic polycarbodiimide according to 1) above, which n may be an integer of 4 to 100 in the formula (1).

4) The aromatic polycarbodiimide according to 1) above, which n may be an integer of 4 to 40 in the formula (1).

5) The aromatic polycarbodiimide according to 1) above, which the aromatic polycarbodiimide may comprise a structure represented by the following formula (2):

$$\left( \bigcirc - O - \underset{(A)_m-Ph}{\bigcirc} - O - \bigcirc - N=C=N \right)_n \tag{2}$$

wherein n is an integer of 2 to 300, m is 0 or 1, A is a divalent organic group having 4 or less carbon atoms, and Ph is a phenyl group.

6) The aromatic polycarbodiimide according to 1) above, which the aromatic polycarbodiimide may comprise a structure represented by the following formula (3):

$$\left( \bigcirc - \underset{CH_3}{\overset{CH_3}{\underset{|}{C}}} - \bigcirc - \underset{CH_3}{\overset{CH_3}{\underset{|}{C}}} - \bigcirc - N=C=N \right)_n \tag{3}$$

wherein n is an integer of 2 to 300.

7) The aromatic polycarbodiimide according to 1) above, which the aromatic polycarbodiimide may comprise a structure represented by the following formula (4):

$$\left( \underset{X}{\overset{X}{\bigcirc}} - CH_2 - \underset{X}{\overset{X}{\bigcirc}} - N=C=N \right)_n \tag{4}$$

wherein n is an integer of 2 to 300, and X's are the same or different halogen atoms.

8) In a second aspect, the present invention provides a polycarbodiimide solution prepared by dissolving the aromatic polycarbodiimide in an organic solvent, wherein the aromatic polycarbodiimide is one selected from the group consisting of 1) to 7) above.

9) In a third aspect, the present invention provides a polycarbodiimide sheet, which comprises as a main ingredient the aromatic polycarbodiimide, wherein the aromatic polycarbodiimide is one selected from the group consisting of 1) to 7) above.

Regarding the aromatic polycarbodiimide having a structure represented by the formula (2), the aromatic polycarbodiimide represented by the following formula (wherein n is an integer, the position of substitution of the two phenoxy group attached to the central benzene ring is 1,3- or 1,4-) is known (Japanese Patent Application Laid-open No. Hei 9-235341). However, there has been no report on the aromatic polycarbodiimide having a substituent on the central benzene ring in the repeating unit of the main chain as in the present invention. By introduction of a substituent on the central benzene ring in the repeating unit of the main chain, the polycarbodiimide of the present invention has improved solubility and heat resistance as compared with the corresponding polymer without such substituents.

Also, regarding the aromatic polycarbodiimide having a structure represented by the formula (4), the polycarbodiimide represented by the following formula (wherein $R_2$ and $R_3$ independently represent a hydrogen atom, a low alkyl group or an alkoxy group, X represents an oxygen atom or a methylene group) is known (Japanese Patent Application Laid-open No. Hei 3-62814). However, there has been no report on the aromatic polycarbodiimide having a halogen atom on the benzene rings in the main chain as in the aromatic polycarbodiimide having a structure represented by the formula (4) of the present invention.

Other objects and advantages of the present invention will become apparent from the detailed description to follow taken in conjunction with the appended claims.

DETAILED DESCRIPTION OF THE PREFERRED EMBODIMENTS

An aromatic polycarbodiimide containing a structure represented by the formula (2) of the present invention is obtained by polymerizing a diisocyanate represented by the following formula (5) as a monomer in the presence of a phosphorus-based catalyst in accordance with a known polymerization method.

In the above formula, A is a divalent organic group having 4 or less carbon atoms, such as a carbonyl group, a vinylene group, a propenylene group, a methylene group, an ethylene group, an ethylidene group, a trimethylene group, a propylene group, an isopropylidene group, a tetramethylene group and the like. Out of these, especially preferred are a carbonyl group, a vinylene group, a propenylene group, a methylene group, an ethylene group, an ethylidene group and an isopropylidene group. In the formula, Ph is a phenyl group, and m is 0 or 1. The polymerization degree n is 2 to 300.

Illustrative examples of the diisocyanate monomer as the raw material of the polycarbodiimide of the present invention include 2-phenyl-1,4-bis(4-isocyanatophenoxy)benzene, 2-benzyl-1,4-bis(4-isocyanatophenoxy)benzene, 2-phenethyl-1,4-bis(4-isocyanatophenoxy)benzene, 2-styryl-1,4-bis(4-isocyanatophenoxy)benzene, 2-cinnamyl-1,4-bis(4-isocyanatophenoxy)benzene, 2-benzoyl-1,4-bis(4-isocyanatophenoxy)benzene, 2-(α,α-dimethylbenzyl)-1,4-bis(4-isocyanatophenoxy)benzene, 2-(α-methylbenzyl)-1,4-bis(4-isocyanatophenoxy)benzene, position isomers having these substituents at different positions and the like.

Although a diisocyanate represented by the following formula (6) is known (Japanese Patent Application Laid-open No. Hei 9-188660), the monomer represented by the above formula (5) is not disclosed.

(wherein, $R_1$, $R_2$ and $R_3$ are independently a lower alkyl group having 1 to 4 carbon atoms or a halogen atom, and l, m', and n are independently an integer of 0 to 4.)

Another process for producing the aromatic polycarbodiimide containing the structure represented by the formula (2) of the present invention comprises diisocyanating an aromatic diamine represented by the following formula (7):

wherein m is 0 or 1, A is a divalent organic group having 4 or less carbon atoms, and Ph is a phenyl group, in accordance with a known isocyanating method, for example, a method which will be described hereinafter, to obtain a compound of the formula (5) and polymerizing the compound.

The aromatic polycarbodiimide containing a structure represented by the formula (3) of the present invention is obtained by polymerizing a diisocyanate represented by the following formula (8):

(8)

as a monomer in the presence of a phosphorus-based catalyst in accordance with a known polymerization method. This diisocyanate is known (CAS Reg. No. 163843-15-0) but there has been no report that an aromatic polycarbodiimide is obtained from this compound.

Another process for producing an aromatic polycarbodiimide containing a structural unit represented by the formula (3) comprises isocyanating an aromatic diamine represented by the following formula (9):

(9)

in accordance with a known isocyanating method, for example, the method which will be described hereinafter, to obtain a compound of the formula (8) and polymerizing the compound.

The aromatic polycarbodiimide containing the structural unit represented by the formula (4) is obtained by polymerizing a diisocyanate as a monomer represented by the following formula (10):

(10)

wherein X's are the same or different halogen atoms, in the presence of a phosphorus-based catalyst in accordance with a known polymerization method.

Although a diisocyanate represented by the following formula (11) is known (Japanese Examined Patent publication No. Sho 47-36278, Japanese Patent Application Laid-open No. Sho 56-50963, Shinde, et al., J. Polym. Mater., 6, 1, 25 (1989), B. M. Shinde, N. D. Ghatge, J. of Polym. Sci., 30, 3505 (1985)), there has been no report that an aromatic polycarbodiimide is obtained from this diisocyanate.

(11)

Another process for producing an aromatic polycarbodiimide containing the structure represented by the formula (4) comprises isocyanating a diamine as a raw material represented by the following general formula (12):

(12)

wherein X's are the same or different halogen atoms, in accordance with a known isocyanating method to obtain a compound of the formula (10) and polymerizing the compound.

Preparation of Diisocyanate from Diamine

To obtain a diisocyanate from a diamine, there is, for example, a method in which phosgene, diphenyl carbonate or carbonyl diimidazole reacts with a diamine. Alternative methods include one in which a halogenated alkyl formate or halogenated aryl formate is caused to act on a diamine compound to synthesize a dicarbamate and the dicarbamate is then diisocyanated using chlorosilane as an activating agent (G. Greber. et al., Angew. Chem. Int. Ed., Vol. 17, No. 12, 941 (1968)) or catechol borane (V. L. K. Valli. et al., J. Org. Chem., Vol. 60, 257 (1995)). They are preferred from the viewpoints of yield and safety.

First, a dicarbamate is produced by reacting methyl chloroformate, ethyl chloroformate, phenyl chloroformate or p-nitrophenyl chloroformate with a corresponding diamine compound. Out of these, phenyl chloroformate or p-nitrophenyl chloroformate is suitable to smoothly proceed with isocyanation. Since p-nitrophenyl chloroformate has high activity and may cause a side reaction, phenyl chloroformate is the most preferred. These halogenated formates may be used alone or in mixture of two or more. The amount of the halogenated formate used is preferably 1.5 to 3.4 times, more preferably 1.8 to 3.0 times the number of moles of the corresponding diamine compound. The amount smaller than 1.5 times is not preferable since an unreacted diamine remains in the system, causing a side reaction with the formed isocyanate to form urea. The amount larger than 3.4 times is not preferable either since it may be difficult to remove unreacted reagents from the system after completion of the reaction, or a side reaction may occur.

Any solvent may be used in the reaction if it dissolves a diamine. Illustrative examples of the solvent include ether-based compounds such as tetrahydrofuran (THF), dioxane and diethyl ether; ketone-based compounds such as acetone, methyl ethyl ketone and methyl isobutyl ketone; ester-based compounds such as ethyl acetate; aromatic hydrocarbon-based solvents such as toluene, xylene and benzene; and halogenated hydrocarbons such as chloroform, methylene dichloride and tetrachloroethylene. These solvents may be used alone or in mixture of two or more.

The concentration of the corresponding diamine in the reaction mixture is generally 1 to 50 wt %, preferably 5 to 40 wt %, the most preferably 10 to 30 wt %. When the concentration of the diamine is lower than 1 wt %, it takes time for the reaction, which is not practical. When the concentration of the diamine is higher than 50 wt %, an undesirable side reaction may occur or it may be difficult to control a reaction.

The reaction temperature is −40 to 100° C., preferably −20 to 80° C., more preferably 0 to 60° C. The reaction temperature lower than −40° C. is not practically acceptable since the reaction does not proceed smoothly. When the reaction temperature is higher than 100° C., a side reaction may occur.

Any base for trapping hydrogen chloride formed by the reaction is acceptable if it dissolves in the solvent used and does not inhibit the reaction. Both organic bases and inorganic bases may be used. Organic bases are preferred from the viewpoint of solubility in a solvent and tertiary amines such as triethylamine, pyridine, 1,8-diazabicyclo[5.4.0]-7-undecene, collidine, picoline and lutidine are particularly preferred because they do not inhibit the reaction. The amount of the base used is preferably 1.5 to 3.4 times, more preferably 1.8 to 3.0 times, the number of moles of the diamine used.

The obtained dicarbamate is purified by recrystallization or a conventionally known means such as a column chromatography. Distillation may be carried out as required.

Diisocyanation of the dicarbamate with an organic silicon halide compound is carried out by thermally decomposing the dicarbamate using the organic silicon halide compound as an activation reagent in an amount 1.5 to 3.4 times, preferably 1.8 to 3.0 times, the number of moles of the dicarbamate. When the amount of the activation reagent is smaller than 1.5 times, the reaction may not proceed completely. When the amount is larger than 3.4 times, it may be difficult to remove an unreacted reagent from the system.

Preferred examples of the organic silicon halide compound include chlorosilanes such as trimethylchlorosilane, dimethyldichlorosilane, methyltrichlorosilane, triethylchlorosilane, trimethoxychlorosilane and tetrachlorosilane, out of which trimethylchlorosilane is particularly preferred from an economical point of view and the viewpoint of ease of handling.

Any solvent may be used in the present invention if it dissolves or suspends the dicarbamate and any one of the above solvents used for the carbamation may be used. These solvents may be used alone or in mixture of two or more. The reaction temperature may be changed by substituting part or all of the solvents during the reaction as the case may be.

The reaction temperature is 0 to 150° C., preferably 20 to 130° C., more preferably 40 to 110° C. When the temperature is lower than 0° C., the reaction does not proceed smoothly and when the temperature is higher than 150° C., it is difficult to select a suitable solvent.

The base for trapping hydrogen chloride formed during the reaction may be the same as the base used for the carbamation and used in the same amount.

The obtained diisocyanate monomer may be purified by a known means such as column chromatography or distillation after the reaction or may be used directly after the excessive reagents and solvent are removed.

Preparation of Polycarbodiimide from Diisocyanate

To prepare the aromatic polycarbodiimide containing the structure represented by the formula (2), the formula (3) or the formula (4) of the present invention, a diisocyanate monomer represented by the formula (5), the formula (8) or the formula (10) may be polymerized alone or may be copolymerized with other organic diisocyanate such as 4,4'-diphenylmethane diisocyanate, 2,6-tolylene diisocyanate, 2,4-tolylene diisocyanate, 1-methoxyphenyl-2,4-diisocyanate, 3,3-dimethoxy-4,4'-diphenylmethane diisocyanate, 4,4'-diphenylether diisocyanate, 3,3'-dimethyl-4,4'-diphenylether diisocyanate, o-tolylene diisocyanate, 2,2-bis[4-(4-isocyanatophenoxy)phenyl] hexafluoropropane, 2,2-bis[4-(4-isocyanatophenoxy) phenyl]propane or the like so long as the characteristics of the aromatic polycarbodiimide of the present invention are not impaired.

The copolymerization proportion of the organic diisocyanates used as comonomer(s) is preferably 1 to 90 mol %, more preferably 1 to 70 mol %, most preferably 1 to 50 mol % based on the diisocyanate monomer represented by the formula (5), (8) or (10). When the copolymerization proportion is larger than 90 mol %, the characteristics of the polycarbodiimide of the present invention may be lost. One or more other polycarbodiimides may be mixed in the form of varnish in a ratio of 1/100 to 100/1 to the aromatic polycarbodiimide of the present invention.

The polymerization temperature is preferably 40 to 150° C., more preferably 50 to 140° C. When the polymerization temperature is lower than 40° C., the reaction time becomes too long, which is not practical. When the polymerization temperature is higher than 150° C., it is difficult to select a suitable solvent.

The concentration of the diisocyanate monomer for the synthesis of a polycarbodiimide is 5 to 70 wt %, preferably 10 to 60 wt %, most preferably 15 to 50 wt % in the case of an aromatic polycarbodiimide containing the structural unit represented by the formula (2), 5 to 70 wt %, preferably 10 to 60 wt % in the case of an aromatic polycarbodiimide containing the structural unit represented by the formula (3), and 2 to 70 wt %, preferably 5 to 60 wt % in the case of an aromatic polycarbodiimide containing a structural unit represented by the formula (4). When the concentration of the monomer is lower than 2 wt %, carbodiimidization may not proceed. When the concentration of the monomer is higher than 70 wt %, it may be difficult to control the reaction.

The organic solvent used for the synthesis of a polycarbodiimide and the organic solvent used in a polycarbodiimide solution may be a known solvent. Illustrative examples of the solvents include halogenated hydrocarbons such as tetrachloroethylene, 1,2-dichloroethane, chloroform and dichloromethane; ketone-based solvents such as acetone, methyl ethyl ketone, methyl isobutyl ketone and cyclohexanone; cyclic ether-based solvents such as tetrahydrofuran and dioxane; and aromatic hydrocarbon-based solvents such as toluene, xylene and ethylbenzene. They may be used alone or mixture of two or more.

A known phosphorus-based catalyst is used as the catalyst used for the carbodiimidization, as exemplified by phospholene oxides such as 1-phenyl-2-phospholene-1-oxide, 3-methyl-2-phospholene-1-oxide, 1-ethyl-2-phospholene-1-oxide, 3-methyl-1-phenyl-2-phospholene-1-oxide or 3-phospholene isomers thereof.

The above carbamation, diisocyanation and carbodiimidization of the diamine may be performed stepwise by carrying out isolation and purification in each step or continuously in a same reactor as a series of reactions.

At any one of the end stage, middle satege or initial stage of a polymerization reaction, or throughout the polymerization reaction, a monoisocyanate may be added to carry out an end-capping treatment. Illustrative examples of the monoisocyanate include phenyl isocyanate, p-nitrophenyl isocyanate, p-tolyl isocyanate, p-formylphenyl isocyanate, p-isopropylphenyl isocyanate, p-trifluoromethylphenyl isocyanate, p-methoxyphenyl isocyanate, p-phenoxyphenyl isocyanate, p-chlorophenyl isocyanate, and isomers having a substituent at the ortho-positions thereof, or isomers having a substituent at the meta-positions thereof, 1-naphthyl isocyanate, 2-naphthyl isocyanate, and other aromatic isocyanates. The thus obtained polycarbodiimide solution has excellent storage stability.

After completion of the reaction, the reaction mixture may be injected into a poor solvent such as methanol, ethanol, hexane, pentane, heptane or isopropyl alcohol to deposit a polycarbodiimide as a precipitate and remove an unreacted monomer and a solvent. To prepare a polycarbodiimide solution, the polymer deposited as a precipitate is washed and dried by predetermined operation and dissolved in an organic solvent again. The stability of the polycarbodiimide solution can be improved by carrying out this operation.

The obtained polymer may be purified by adsorbing a by-product contained in the polymer solution to an appropriate adsorbent. Illustrative examples of the adsorbent include alumina gel, silica gel, activated carbon, zeolite, active magnesium oxide, active bauxite, fuller's earth, activated china clay, molecular sieving carbon and the like. They may be used alone or in combination thereof.

The polycarbodiimide of the present invention is a polycarbodiimide of the formula (1) in which n is an integer of 2 to 300, preferably 4 to 100, more preferably 4 to 40. When the polymerization degree n of the polycarbodiimide is larger than 300, it is readily gelled in several minutes to several hours while it is left to stand at normal temperature, which is not preferred for practical application. When the polymerization degree n is less than 2, the coating film lacks reliability, which is not preferable.

The number average molecular weight of the aromatic polycarbodiimide of the present invention containing the structural unit represented by the formula (3) is preferably 700 to 35,200, more preferably 1,000 to 14,000. That is, in the formula (1), n is preferably an integer of 2 to 100, more preferably 3 to 40.

Production of Film and Adhesive Sheet

The polycarbodiimide film (or sheet) of the present invention is obtained by forming polycarbodiimide varnish into a film having an appropriate thickness in accordance with a known method (such as casting, spin coating, roll coating or the like). This film may be dried usually at a temperature required to remove the solvent. To ensure that a curing reaction does not proceed so far, the coating temperature is, for example, 20 to 350° C., preferably 50 to 300° C., most preferably 70 to 250° C. in the case of an aromatic polycarbodiimide containing the structural unit represented by the formula (2), for example, 20 to 350° C., preferably 50 to 300° C. in the case of an aromatic polycarbodiimide containing a structural unit represented by the formula (3) and, for example, 20 to 350° C., preferably 50 to 250° C. in the case of an aromatic polycarbodiimide containing a structural unit represented by the formula (4). When the drying temperature is lower than 20° C., the solvent remains in the film with the result that the obtained film has poor reliability, which is not preferable. When the drying temperature is higher than 350° C., the heat curing of the film readily proceeds, which is not preferable.

The polycarbodiimide resin composition of the present invention may contain fine inorganic filler in amounts within the range where its workability and heat resistance may not be impaired. Various kinds of additives such as a smoothing agent, leveling agent and defoaming agent may be added as required to provide surface smoothness.

A film formed molded article molded from the aromatic polycarbodiimide of the present invention may be used as a heat resistant adhesive sheet. The thickness of film or adhesive sheet molded from the aromatic polycarbodiimide is generally 1 to 200 μm but is not limited to this range and may be suitably selected according to the purpose. The shape and size of a sheet may be suitably determined according to an adherend such as a lead frame or semiconductor chip.

When an adhesive sheet is to be produced, at least one selected from metals such as aluminum, copper, silver, gold, nickel, chromium, lead, tin, zinc, palladium and solder, or alloys thereof, ceramics such as alumina, silica, magnesia and silicon nitride, and various carbon inorganic powders may be blended optionally to provide conductivity, improve heat conductivity and control elastic modulus, especially to increase elastic modulus.

Further, the film may be formed on a substrate film to produce an adhesive sheet. To produce such an adhesive sheet, the substrate film may be coated with varnish, or a film is formed and laminated with a substrate film by pressing.

The substrate film used herein is a metal foil or insulating film. The metal foil may be a foil of aluminum, copper, silver, gold, nickel, indium, chromium, lead, tin, zinc, palladium or the like. They may be used alone or as an alloy. Any film of a polyimide, polyester or polyethylene terephthalate may be used as the insulating film if it has heat resistance and chemical resistance.

The metal foil and the insulating film may be used alone or laminated together into a double-layer substrate, for example a metal foil/insulating film. This double-layer substrate is, for example, a copper/polyimide double-layer substrate.

The sheet adhesive of the present invention exhibits strong adhesive force and becomes a cured product having low hygroscopicity when it is cured by a heat treatment. To carry out the heat treatment, a suitable means such as a heater, ultrasonic wave or ultraviolet radiation may be used. Therefore, the adhesive sheet of the present invention is preferably used in the adhesion treatment of various materials. Particularly, the adhesive sheet of the present invention is preferably used in the fixing treatment of electric and electronic parts typified by semiconductor chips and lead frames, which require highly reliable fixing treatment and hence, must have low hygroscopicity. The adhesive sheet of the present invention is excellent in such points that it has low hygroscopicity, high flexibility which makes handling easy, excellent adhesion to a semiconductor device, high storage stability and a low dielectric constant.

(Application)

The aromatic polycarbodiimide of the present invention can also be used as an adhesive for electronic parts making use of its heat resistance.

EXAMPLES

The following examples and comparative examples are given to further illustrate the present invention. All the reactions were carried out in a nitrogen atmosphere. The diamines used as a starting material in Examples 1, 2, and 4 were each synthesized according to the methods described in the literature (U.S. Pat. No. 4,576,857, and Chem. Ind. 62, 503 (1995)). In Comparative Example 1 and Example 9, the diamines used as a starting material were obtained from Wakayama Seika Kogyo Co., Ltd. In Comparative Examples 2 and 3, the diisocyanates used as a starting material were obtained from Nippon Polyurethane Kogyo Co., Ltd. The characteristics of the obtained aromatic polycarbodiimides and sheets (films) prepared therefrom were measured as follows.

(IR)

Measured using an infrared spectrophotometer (trade name: FT/IR-230, manufactured by JEOL Ltd.).

(Heat curing temperature (Tc))

Measured using a differential scanning calorimeter (trade name: DSC-200, manufactured by Seiko Instruments, Inc.) and the exothermic peak of trimerization is taken as heat curing temperature.

(Number average molecular weight)

Measured using a gel permeation chromatograph (trade name: HLC8120, manufactured by Tosoh Corporation), a column (trade name: $GMH_{HR-H}+GMH_{HR-H}+G2000H_{HR}$, manufactured by Tosoh Corporation), tetrahydrofuran as a developing solvent and polystyrene as a standard substance.

(Adhesive strength)

Peel strength at 180° was measured by grasping a copper foil and a 42 alloy plate and separating them at room temperature using a tensile tester (trade name: Shimadzu Autograph AGS-100D, manufactured by Shimadzu Corporation).

(Glass transition temperature (Tg))

Measured using a thermomechanical analyzer (trade name: TMA/SS100, manufactured by Seiko Instruments, Inc.).

(Elastic modulus (E'))

Measured using a dynamic viscosity measuring apparatus (trade name: DMS210, manufactured by Seiko Instruments, Inc.).

(Storage stability of varnish)

This is expressed as the number of days during which no gelling of varnish nor increase in viscosity occurs when the varnish is left to stand at room temperature.

Example 1

2-Phenyl-1,4-bis(4-aminophenoxy)benzene (20 g, 54.28 mmol), triethylamine (10.99 g, 108.56 mmol) and 156.5 g of toluene were charged into a 500-ml four-neck flask equipped with a stirrer, a dropping funnel, a reflux condenser and a thermometer. The flask was cooled in an iced bath and phenyl chloroformate (17.00 g, 108.56 mmol) was dropped stepwise over 1 minute from the dropping funnel. Thereafter, the mixture was stirred at room temperature for 120 minutes.

After the formation of a carbamate was confirmed by IR, trimethylchlorosilane (11.79 g, 108.5 mmol), triethylamine (10.99 g, 108.56 mmol) and a carbodiimidization catalyst (3-methyl-1-phenyl-2-phospholene-1-oxide) (521.6 mg, 2.714 mmol) were charged and stirred at 60° C. for 1 hour and then at 80° C. for 4 hours to carry out isocyanation and polymerization.

Figure 1:
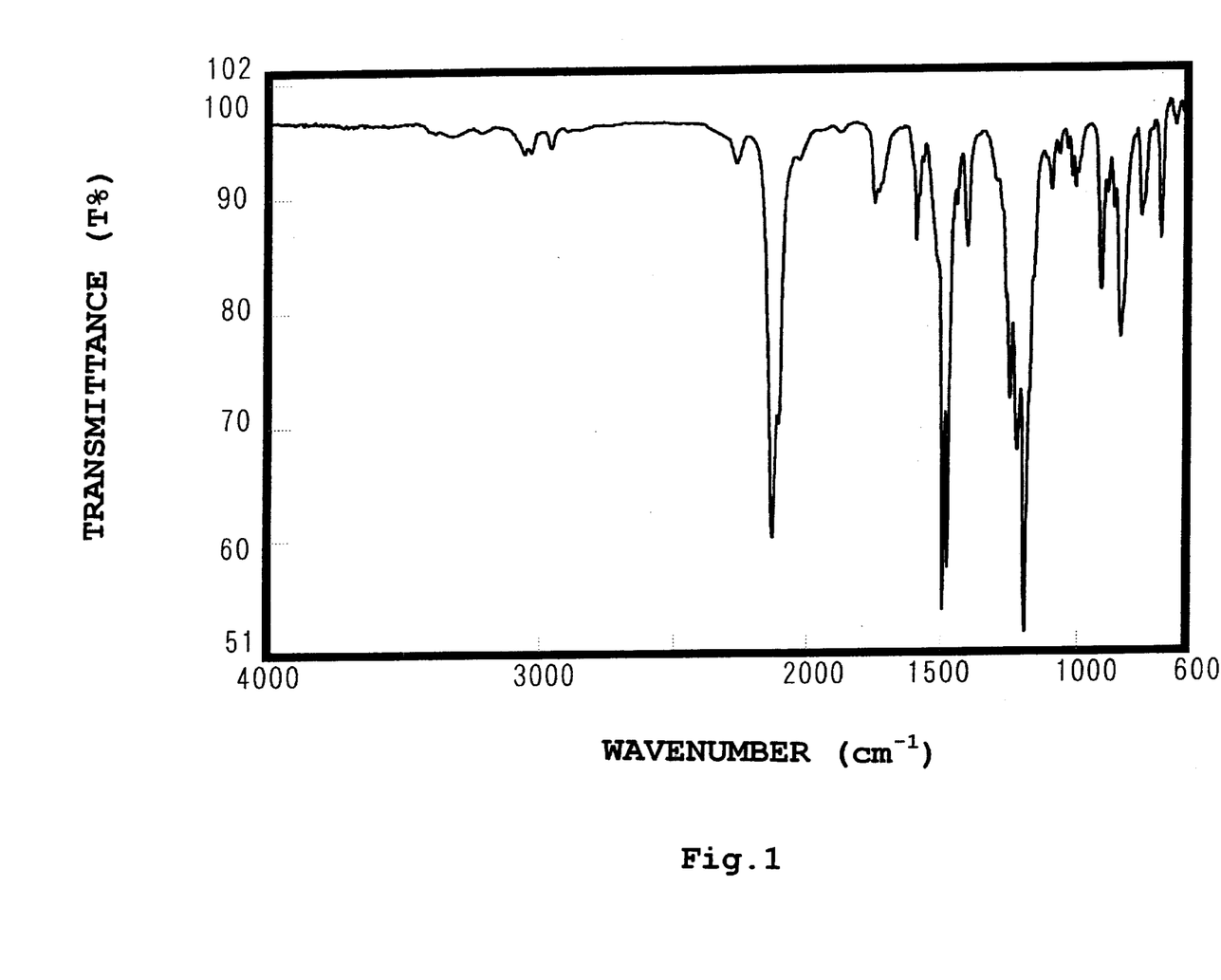
FIG. 1 is a chart illustrating an infrared absorption spectrum of an aromatic polycarbodiimide obtained in Example 1.

Carbodiimidization was confirmed from an IR spectrum shown in FIG. 1 and the formed triethylamine hydrochloride was removed by filtration to obtain varnish. The number average molecular weight (Mn) of this aromatic polycarbodiimide was 2,350 (n=6).

The storage stability of the above varnish was 10 days or more. The varnish was cast onto a glass plate and dried at 90° C. for 30 minutes and then at 250° C. for 30 minutes to obtain a 17 μm-thick film having flexibility. When the thermal properties of the obtained film were evaluated, its heat curing temperature was 330° C., glass transition temperature was 203° C. and elastic modulus at room temperature was 3.0 GPa.

Powders obtained by reprecipitating the varnish with an isopropyl alcohol, collecting the deposited solids and drying them could be redissolved in a general organic solvent such as toluene, tetrahydrofuran, cyclohexanone or chloroform.

Example 2

An aromatic polycarbodiimide was synthesized in the same manner as in Example 1 except that 2-(α,α-dimethylbenzyl)-1,4-bis(4-aminophenoxy)benzene (54.28 mmol) was used as a diamine to obtain varnish.

Aromatic polycarbodiimide powders having a number average molecular weight of 3,500 (n=8) were obtained by reprecipitating the varnish with an isopropyl alcohol, collecting the deposited solids and drying them.

The storage stability of the varnish was 10 days or more. The varnish was cast onto a glass plate and dried at 90° C. for 30 minutes and further at 250° C. for 30 minutes to obtain a 17 μm-thick film having flexibility. When the thermal properties of the obtained film were evaluated, its heat curing temperature was 330° C., glass transition temperature was 190° C. and elastic modulus at room temperature was 2.5 GPa.

Powders obtained by reprecipitating the varnish with an isopropyl alcohol, collecting the deposited solids and drying them could be redissolved in a general organic solvent such as toluene, tetrahydrofuran, cyclohexanone or chloroform.

Comparative Example 1

A polycarbodiimide was synthesized in the same manner as in Example 1 except that 1,4-bis(4-aminophenoxy) benzene (54.28 mmol) was used as a diamine to obtain varnish.

Aromatic polycarbodiimide powders having a number average molecular weight of 1,900 (n=6) were obtained by reprecipitating the varnish with an isopropyl alcohol, collecting the deposited solids and drying them. The powders were soluble in a polar solvent such as tetrahydrofuran in a low concentration but insoluble in a non-polar solvent such as toluene.

Comparative Example 2

5.0 g (28.7 mmol) of a mixture of 2,4-tolylene diisocyanate and 2,6-tolylene diisocyanate (mixing rate of 90:10) was stirred in 20 g of tetrahydrofuran together with 43 mg (0.22 mmol) of a carbodiimidization catalyst (3-methyl-1-phenyl-2-phospholene-1-oxide) at 60° C. for 15 hours to obtain a polycarbodiimide solution. The number average molecular weight of this polycarbodiimide was 6,700 (n=52).

This polycarbodiimide solution was cast onto a glass plate and dried at 90° C. for 30 minutes to produce a 17 μm-thick film having a glass transition temperature Tg of 53° C. When this film was further heated at 250° C. for 30 minutes, it changed its color and lost flexibility and self holding properties. When the thermal properties of this film were evaluated, its heat curing temperature was 300° C., glass transition temperature was 227° C. and elastic modulus at room temperature was 3.9 GPa.

Example 3

The polycarbodiimide films obtained in Examples 1 and 2 and Comparative Example 2 were each placed on a copper foil, a 42 Alloy plate (Ni:Fe et al.=40.0–43.0:60.0–57.0 alloy plate, trade name: NAS 42, manufactured by Nippon Yakin Kogyo K.K.) was placed on the polycarbodiimide films and pressed with an electric heat press at a temperature of 250° C. and a pressure of 50 kg/cm² for 1 second to prepare laminate samples a, b and c. The measurement results of peel strengths and solder resistances of the samples a, b and c are shown in the table below.

TABLE 1

| Sample | Polycarbodiimide | Peel Strength (g/cm) | Solder Resistance (260° C. × 10 seconds) |
| --- | --- | --- | --- |
| a | Example 1 | 1200 | not swollen |
| b | Example 2 | 1400 | not swollen |
| c | Comparative Example 2 | 50 | swollen |

The samples a and b prepared by laminating the aromatic polycarbodiimide films of the present invention on a substrate were superior in both peel strength and solder resistance, whereas the sample c prepared by laminating the polycarbodiimide film of Comparative Example 2 was inferior in both peel strength and solder resistance.

Example 4

1,4-Bis(4-aminophenylisopropylidene)benzene (17 g, 49.35 mmol), triethylamine (9.99 g, 98.70 mmol) and 146.24 g of tetrahydrofuran were charged into a 500-ml four-neck flask equipped with a stirrer, a dropping funnel, a reflux condenser and a thermometer. The flask was cooled in an iced bath and phenyl chloroformate (15.45 g, 98.70 mmol) was added stepwise over 1 minute from the dropping funnel. Thereafter, these components were stirred at room temperature for 120 minutes.

After the formation of a carbamate was confirmed by IR, trimethylchlorosilane (10.72 g, 98.70 mmol), triethylamine (9.99 g, 98.70 mmol) and a carbodiimidization catalyst (3-methyl-1-phenyl-2-phospholene-1-oxide) (474.2 mg, 2.47 mmol) were charged and stirred at 60° C. for 1 hour and then at 67° C. for 7 hours to carry out isocyanation and polymerization.

Figure 2:
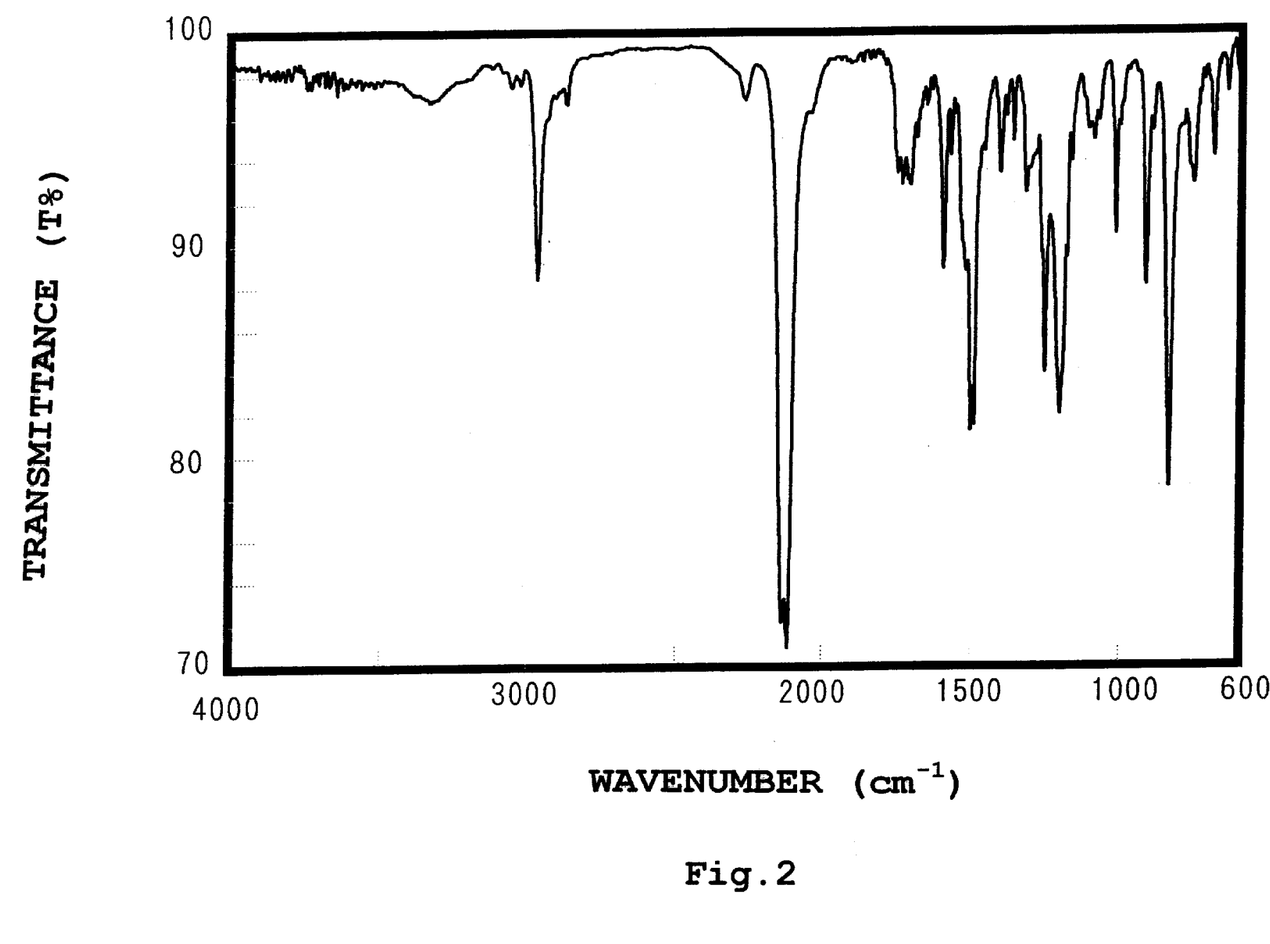
FIG. 2 is a chart illustrating an infrared absorption spectrum of an aromatic polycarbodiimide obtained in Example 4.

Carbodiimidization was confirmed from an IR spectrum shown in FIG. 2 and the formed triethylamine hydrochloride was removed by filtration to obtain varnish. The number average molecular weight (Mn) of this aromatic polycarbodiimide was 1,380 (n=4).

The storage stability of the above varnish was 30 days or more. The varnish was cast onto a glass plate and dried at 90° C. for 30 minutes and then at 250° C. for 30 minutes to obtain a 17 μm-thick film having flexibility. When the thermal properties of the obtained film were evaluated, its glass transition temperature (Tg) was 220.8° C. and elastic modulus at room temperature was 1.65 GPa.

Example 5

1,3-Bis(4-aminophenylisopropylidene)benzene (25.25 g, 73.4 mmol), triethylamine (14.85 g, 146.8 mmol) and 215.3 g of toluene were charged into a 500-ml four-neck flask equipped with a stirrer, a dropping funnel, a reflux condenser and a thermometer. The flask was cooled in an iced bath and phenyl chloroformate (22.98 g, 146.8 mmol) was added stepwise over 0.1 minute from the dropping funnel. Thereafter, the mixture was stirred at room temperature for 120 minutes.

After the formation of a carbamate was confirmed by IR, trimethylchlorosilane (14.34 g, 132 mmol), triethylamine (13.35 g, 132 mmol) and a carbodiimidization catalyst (3-methyl-1-phenyl-2-phospholene-1-oxide) (0.704 mg, 3.67 mmol) were charged and stirred at 60° C. for 1 hour and then at 90° C. for 10 hours to carry out isocyanation and polymerization.

Figure 3:
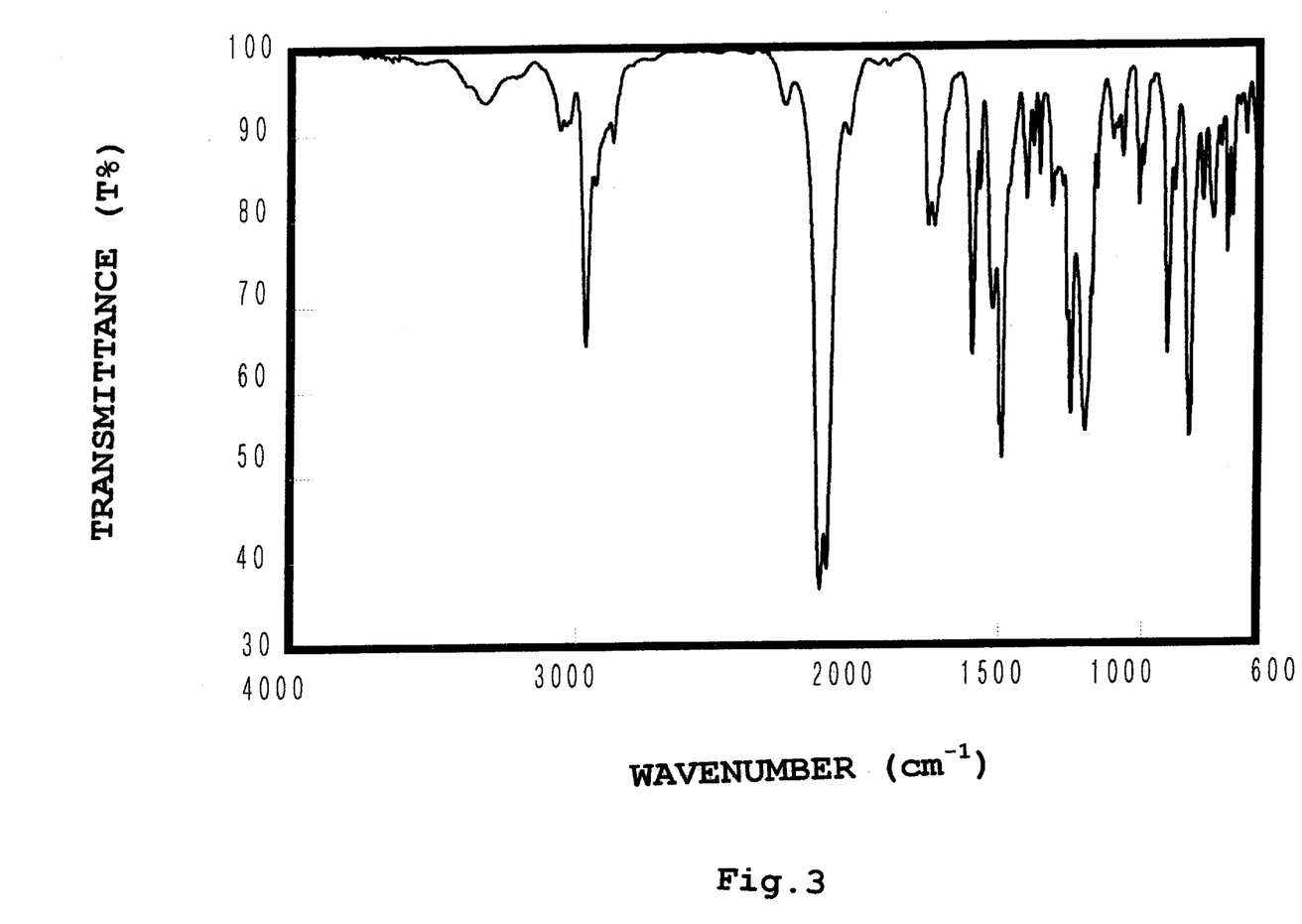
FIG. 3 is a chart illustrating an infrared absorption spectrum of an aromatic polycarbodiimide obtained in Example 5.

Carbodiimidization was confirmed from an IR spectrum shown in FIG. 3 and the formed triethylamine hydrochloride was removed by filtration to obtain varnish. The number average molecular weight (Mn) of this aromatic polycarbodiimide was 1,460 (n=4).

The storage stability of the above varnish was 10 days or more. The varnish was cast onto a glass plate and dried at 90° C. for 30 minutes and then at 250° C. for 30 minutes to obtain a 17 μm-thick film having flexibility. When the thermal properties of the obtained film were evaluated, its glass transition temperature (Tg) was 169.9° C. and elastic modulus at room temperature was 2.47 GPa.

Example 6

The varnish produced in Example 4 was coated on a 105 μm-thick copper foil and dried at 90° C. for 30 minutes and then at 250° C. for 30 minutes to obtain an adhesive sheet having an adhesive layer of 30 μm in thickness. The adhesive layer surface of this adhesive sheet was placed on a 42 alloy plate and pressed at a temperature of 300° C. and a pressure of 50 kg/cm² for 1 second to obtain a laminate sheet. When the adhesive strength of this laminate sheet was measured, it exhibited an adhesive strength of 1,200 g/cm. When the solder resistance of this laminate sheet was tested (260° C.×10 min), it showed good adhesion without swelling. The adhesive layer had a glass transition temperature Tg of 220.8° C., an elastic modulus E' (240° C.) of 0.57 GPa and a water absorption of 0.1%.

Example 7

The varnish produced in Example 5 was coated on a 105 μm-thick copper foil and dried at 90° C. for 30 minutes and then at 250° C. for 30 minutes to obtain an adhesive sheet having an adhesive layer of 30 μm in thickness. The adhesive layer surface of this adhesive sheet was bonded onto a 42 alloy plate and pressed at a temperature of 300° C. and a pressure of 50 kg/cm² for 1 second to obtain a laminate sheet. When the adhesive strength of this laminate sheet bonded onto the substrate was measured, it exhibited an adhesive strength of 1,100 g/cm. When the solder resistance of this laminate sheet comprising the substrate was tested (260° C.×10 sec), it showed good adhesion without swelling. The adhesive layer had a glass transition temperature Tg of 169.9° C., an elastic modulus E' (240° C.) of 0.80 GPa, and a water absorption of 0.1%.

Example 8

The varnish of each of the aromatic polycarbodiimides synthesized in Examples 4 and 5 and Comparative Example 2 was formed into a sheet and gold was deposited in the form of a disk of 2 cm in diameter on one side of the sheet and also on the entire surface of the other side of the sheet to form electrodes so as to measure dielectric constant using the 4284A Precision LCR Meter manufactured by Hewlett Packard Co., Ltd. The results are shown in Table 2.

TABLE 2

|  | Example 4 | Example 5 | Comparative Example 2 |
| --- | --- | --- | --- |
| Dielectric constant (1 MHz) | 2.83 | 2.78 | 3.30 |

As is obvious from Table 2, Examples 4 and 5 which used the aromatic polycarbodiimide of the present invention had a lower dielectric constant than that of the sheet of Comparative Example 2.

Example 9

3,3'-Dichloro-4,4'-diaminodiphenylmethane (14.00 g, 52.41 mmol), triethylamine (10.61 g, 104.81 mmol) and 155.29 g of tetrahydrofuran were charged into a 500-ml four-neck flask equipped with a stirrer, a dropping funnel, a reflux condenser and a thermometer. The flask was cooled in an iced bath and phenyl chloroformate (16.41 g, 104.81 mmol) was added stepwise over 5 minute from the dropping funnel. Thereafter, the mixture was stirred at room temperature for 120 minutes.

After the formation of a carbamate was confirmed by IR, trimethylchlorosilane (11.39 g, 104.81 mmol), triethylamine (10.61 g, 104.81 mmol) and a carbodiimidization catalyst (3-methyl-1-phenyl-2-phospholene-1-oxide) (503.6 mg, 2.620 mmol) were charged and stirred at 60° C. for 1 hour and then at 67° C. for 3 hours to carry out isocyanation and polymerization.

Figure 4:
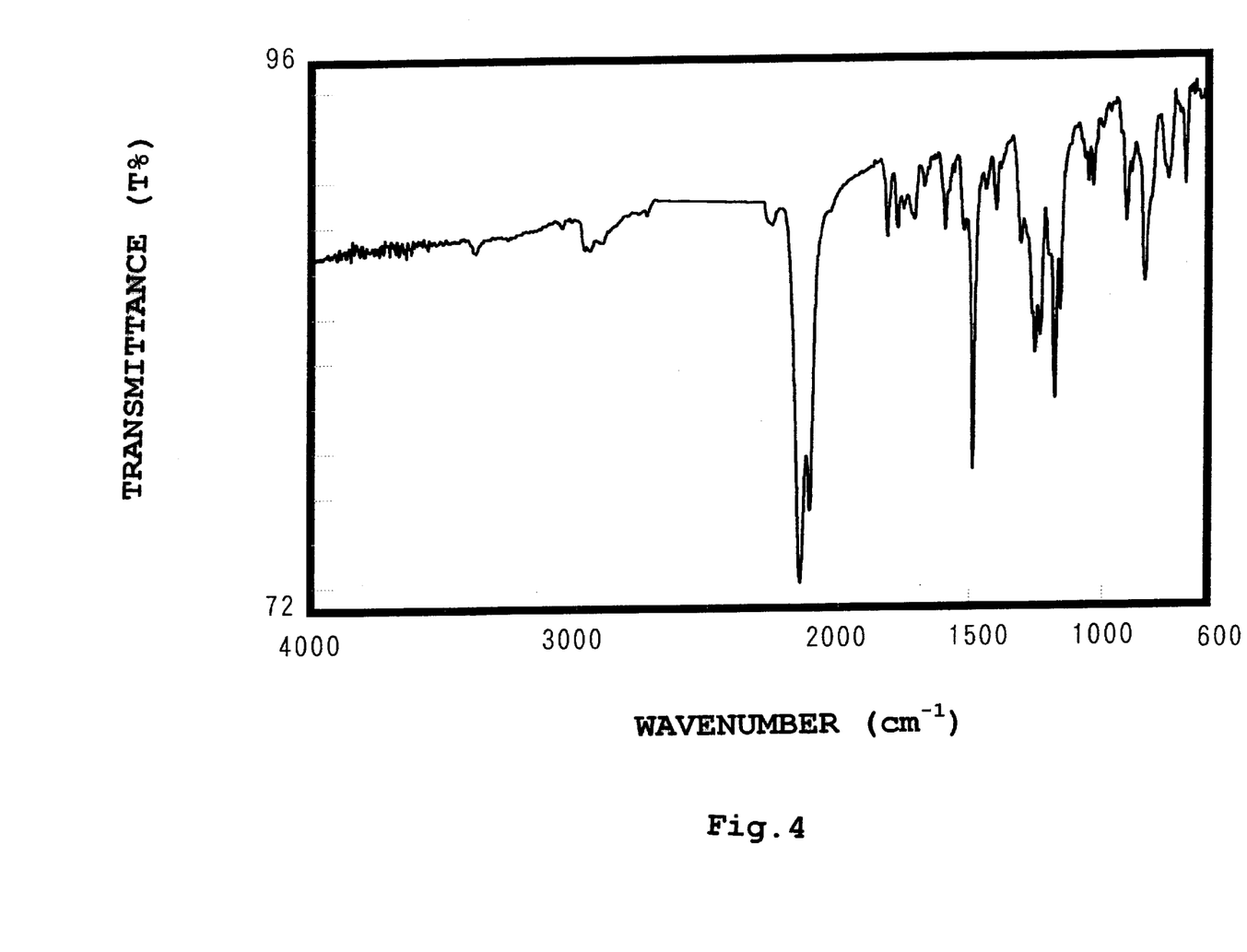
FIG. 4 is a chart illustrating an infrared absorption spectrum of an aromatic polycarbodiimide obtained in Example 9.

Carbodiimidization was confirmed from an IR spectrum shown in FIG. 4 and the formed triethylamine hydrochloride was removed by filtration to obtain varnish. The number average molecular weight (Mn) of this aromatic polycarbodiimide was 1,830 (n=7).

Powders obtained by reprecipitating the varnish with an isopropyl alcohol, collecting the deposited solids and drying them had a glass transition temperature Tg of 62° C. and a heat curing temperature Tc of 380° C.

The storage stability of the above varnish was 7 days or more. The varnish was cast onto a glass plate and dried at 90° C. for 30 minutes and then at 250° C. for 30 minutes to obtain a 17 μm-thick film having flexibility.

Comparative Example 3

4.1 g (16.5 mmol) of 4,4'-diphenylmethane diisocyanate was stirred in 40 g of tetrahydrofuran together with 30 mg (0.156 mmol) of a carbodiimidization catalyst (3-methyl-1-phenyl-2-phospholene-1-oxide) at 60° C. for 15 hours to obtain a polycarbodiimide solution. The number average molecular weight of this polymer was 9,600 (n=37).

The polycarbodiimide solution was cast onto a glass plate and dried at 90° C. for 30 minutes to form a 30 μm-thick film. The obtained film had a heat curing temperature Tc of 300° C. and a glass transition temperature Tg of 78° C. When this film was further heated at 250° C. for 30 minutes, it changed its color and lost flexibility.

The polycarbodiimide of the present invention has high solubility in an organic solvent, high workability, excellent adhesion, heat resistance and moisture resistance, and a low dielectric constant, and can be used as a heat resistant coating material in a soldering step in the production of electronic parts. Improvement of flame retardancy is expected by introducing a halogen atom into the polycarbodiimide.

The present invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. An aromatic polycarbodiimide comprising a structure represented by the following formula (1):

wherein Q is one selected from the group consisting of —$CH_2$—, m is 0 or 1, A is a divalent organic group having 4 or less carbon atoms, Ph is a phenyl group, X's are a hydrogen atom when Q is and the same or different halogen atoms when Q is —$CH_2$—, and n is an integer of 2 to 300.

2. The aromatic polycarbodiimide according to claim 1, wherein the structure represented by the above formula (1) is contained in an amount of more than 10 mol %.

3. The aromatic polycarbodiimide of claim 1, wherein n is an integer of 4 to 100 in the formula (1).

4. The aromatic polycarbodiimide of claim 1, wherein n is an integer of 4 to 40 in the formula (1).

5. The aromatic polycarbodiimide according to claim 1, wherein the aromatic polycarbodiimide comprises a structure represented by the following formula (2):

wherein n is an integer of 2 to 300, m is 0 or 1, A is a divalent organic group having 4 or less carbon atoms, and Ph is a phenyl group.

6. The aromatic polycarbodiimide according to claim 1, wherein the aromatic polycarbodiimide comprises a structure represented by the following formula (3):

(3)

wherein n is an integer of 2 to 300.

7. The aromatic polycarbodiimide according to claim 1, wherein the aromatic polycarbodiimide comprises a structure represented by the following formula (4):

(4)

wherein n is an integer of 2 to 300, and X's are the same or different halogen atoms.

8. A polycarbodiimide solution prepared by dissolving the aromatic polycarbodiimide according to claim 1 in an organic solvent.

9. A polycarbodiimide sheet, comprising as a main ingredient the aromatic polycarbodiimide according to claim 1.

* * * * *